United States Patent [19]

Anderson et al.

[11] Plant 4,953

[45] Nov. 23, 1982

[54] PISTACHIO TREE

[76] Inventors: Henry P. Anderson; Kenneth L. Puryear, both of Pioneer Nursery, 800 N. Chester, Bakersfield, Calif. 93308

[21] Appl. No.: 286,872

[22] Filed: Jul. 27, 1981

[51] Int. Cl.[3] ..... A01H 5/03

[52] U.S. Cl. ..... Plt./30

[58] Field of Search ..... Plt./30

*Primary Examiner*—Robert E. Bagwill

[57] ABSTRACT

This invention relates to a new and distinct variety of pistachio tree primarily identified by its rounded upright growth habit, pleasing green color of mature foliage and its production of female flowers and seed.

8 Drawing Figures

1

The present invention relates to a new and distinct variety of pistachio tree, the variety being primarily characterized, as to novelty, by vigorous, rounded upright growth habit and the abundant production of female (pistillate) flowers and seeds.

The variety is further characterized by abundant foliage of pleasing medium green color and the production of seeds useful for planting to grow understocks upon which commercial nut bearing pistachio varieties may be budded or grafted.

A tree which is vigorous, of rounded upright shape with semi-glossy to matte foliage with pointed leaflets; the flowers being borne in slender clusters or bunches similar to grapes (see photo).

A tree which has a normal height of 15 to 20 feet when mature and a spread about equal to height or less (see photo).

A plant which grows and flowers satisfactorily in any well drained oil and which, when pollenized with a selected male variety, produces seeds useful for growing nursery understocks upon which to bud or graft commercial nut bearing varieties.

Variety name:

*Identification number.*—PN-17-F.

The present variety of pistachio was originated by us at our orchards located at Delano, Kern County, Calif., under conditions of careful control and observation, as a selection from numerous seedlings of several species and hybrids being grown and tested at the time in our search for improved pistachio understocks on which to bud or graft commercial nut bearing varieties.

Subsequent to origination of the variety we successfully asexually reproduced it at our orchard/nursery, located as aforesaid, by budding and by grafting, the reproductions having run true in all respects.

The color photographs illustrate the variety, including (1) mature tree, (2) foliage and (3) flower clusters (photo of flower clusters made on Mar. 14, 1981).

Referring now specifically to the new and distinct variety of pistachio tree, the following is a detailed description thereof in outline; all major color plate identifications, if any, being by reference to the British Colour Council Horticultural Colour Chart, except where common terms of color definition are employed.

Flowers borne in elongated clusters of many individual female flowers, similar to a bunch of grapes (see photo).

2

Quantity of bloom: Abundant.

Buds: Very small in size and of brownish color.

*Bloom size when fully open.*—Very small, with flowers opening at random over period of several days to assure as complete pollenation as possible.

*First flowering of subject variety.*—Identified as PN-17-F — began on Feb. 26, 1981 (as compared with the pollenizer (PN-46-M) which started to flower on Feb. 23, 1981). When said male variety was in peak bloom (February 28) subject female variety was out approximately 15%. On March 14, when male pollenizer bloom was 99% over the subject female (PN-17-F) was 85% over, thus there is sufficient overlap of flowering to assure adequate pollenation to effect a good seed crop.

Seeds resulting from the above male and female crosses produce hybrid seedling understocks of great uniformity and rapid growth.

See photos of seedlings grown from variety PN-17-F×PN-46-M indicating value of present variety as a parent:

A. Uniformity of hybrid seedling as grown in nursery and photographed in October 1980.

B. Red top growth, characteristic of these hybrid seedlings.

C. Young trees, same age (one year), grown under same cultural conditions; Left — Hybrid seedling (PN-17-F×PN-46-M). Right — P. atlantica (species).

D. Same tree as above (c) with soil removed from roots.

Said seedling understocks are apparently much less susceptible to verticillium wilt disease, particularly SS 4, and T1 (cotton strains), which has caused extensive loss of commercial orchard trees budded or grafted on other commonly used pistachio understocks.

Color:

*Flower cluster.*—From tree in seed orchard, Delano, Calif. — main stem of bunch and smaller side branches are medium green, sometimes shaded or tinted brownish.

*Flowers.*—Pinkish.

Reprodictive organs: All female.

*Pistil.*—Small, short.

*Stigma.*—Well formed.

*Fruit (nuts) borne in loose elongated clusters.*—Small.

For comparison — see photo of seeds (4):

*Upper right.*—*Pistachio atlantica* (a commonly used understock).

*Upper left.*—Seeds of subject variety (PN-17-F).

*Bottom.*—Seed and in shell nuts of 'Kerman' variety.

Foliage:

*Leaves.*—Compound of twelve (sometimes more or less).

*Leaflets.*—Medium small, leathery, semi-glossy to matte. Shape: long narrow (lanceolate); apex acute; base acute but less so than apex. Color: medium to dark green, near Spinach Green 0960; new growth — normal (medium) green often tinted reddish, especially young leaves on tips of shoots. Ribs (center) of leaves and center rib of leaflets usually slightly lighter green color than rest of leaf surface. Length of leaves: (including petiole and leaflets) may average about 9–10 inches (or more) — to end of midrib, 7 to 8 inches. Individual leaflets may be up to 4 inches in length.

*Growth.*—Habit — upright when young, becoming much branched and upright to spreading at maturity. Tree usually inclined to have central leader plus several main branches. These main branches support numerous lesser limbs and branches to form a dense symmetrical crown or head.

*Color.*—Main branches and limbs — gray to brownish.

The new variety of pistachio tree as herein described may vary in slight detail due to climatic, soil and cultural conditions under which the variety may be grown, the present description being of the variety as grown at Delano, Calif.

The following is claimed:

1. A new and distinct variety of pistachio tree, identified as PN-17-F, characterized by a mature tree of rounded upright shape, having several main branches and usually a central leader; rapid growth, abundant, leathery foliage, ease of propagation by budding or grafting; and further characterized by the abundant production of female flowers, in clusters, followed by seeds which are especially desirable for planting when pollenized by the male variety, identified as PN-46-M, said hybrid seeds producing a fast growing, disease resistant tree of value for use as understock upon which to bud or graft commercial nut bearing varieties of pistachio such as 'Kerman'.

* * * * *

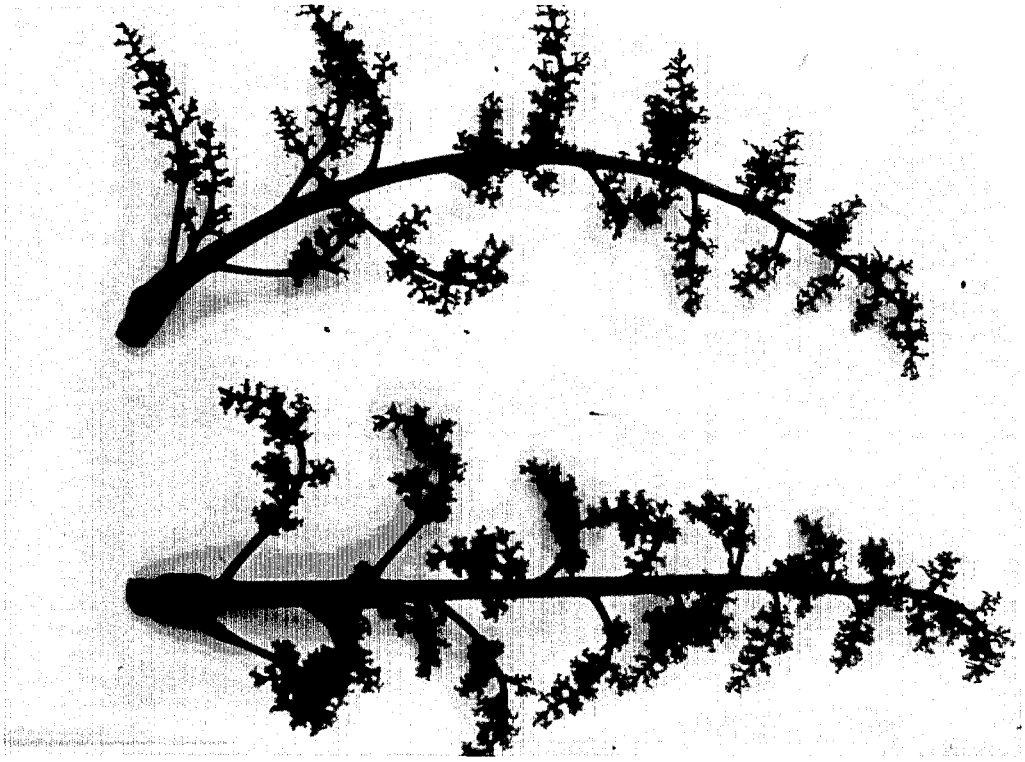
3
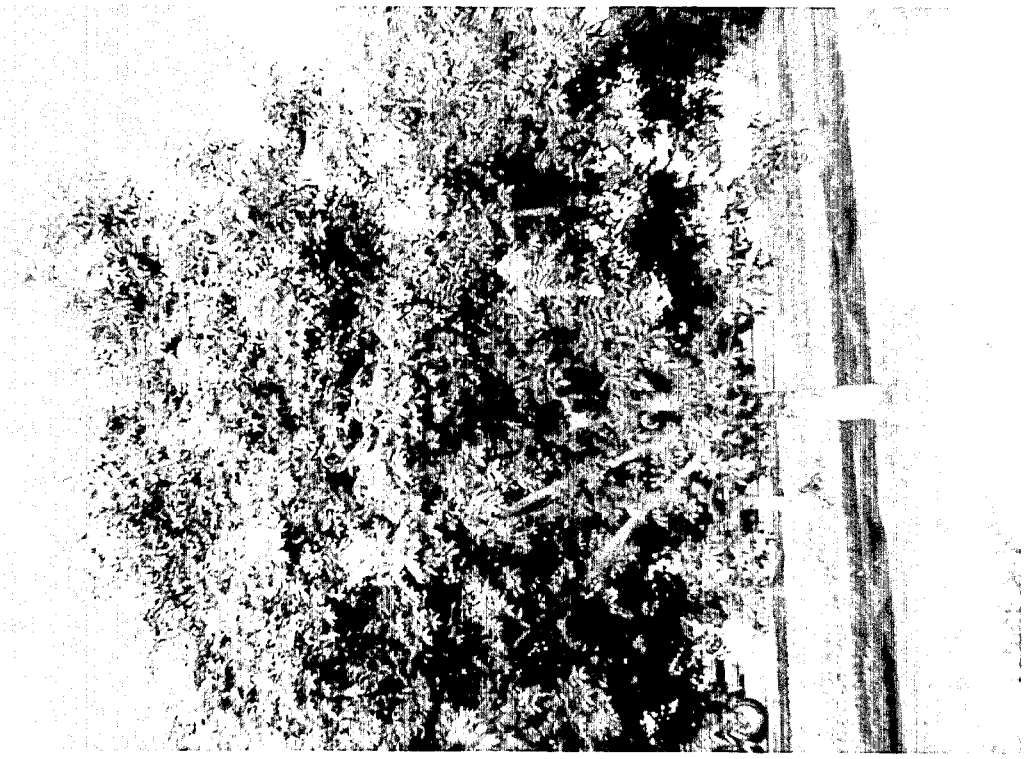
1

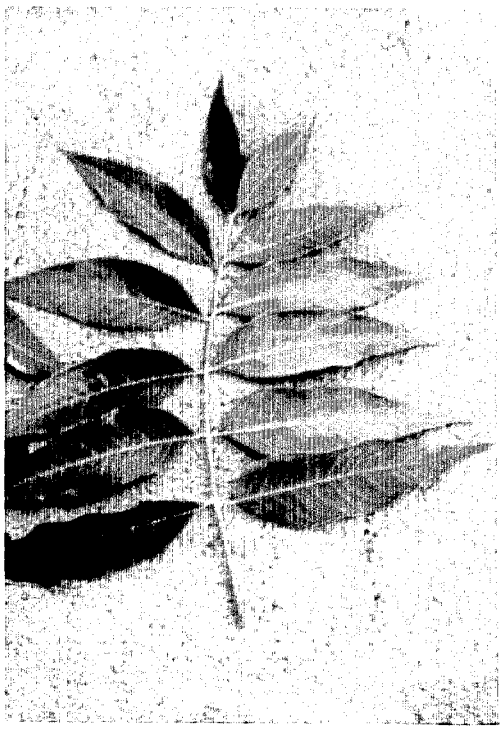
2
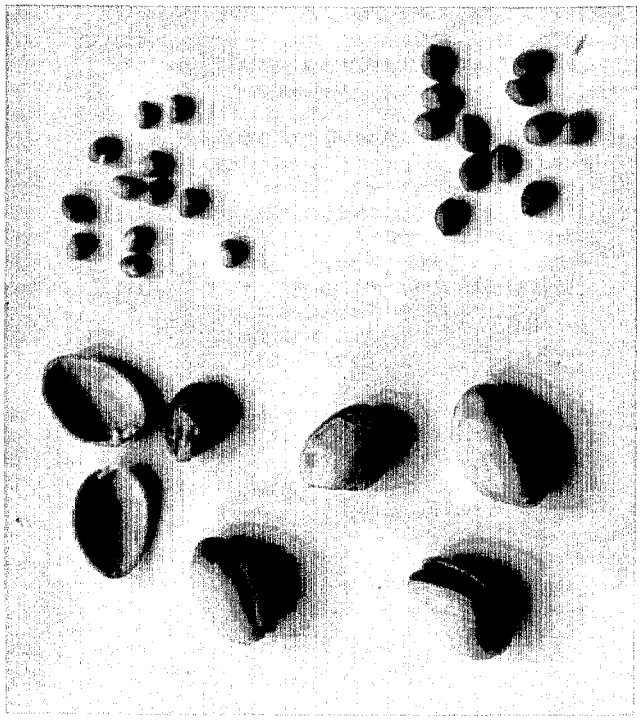
4

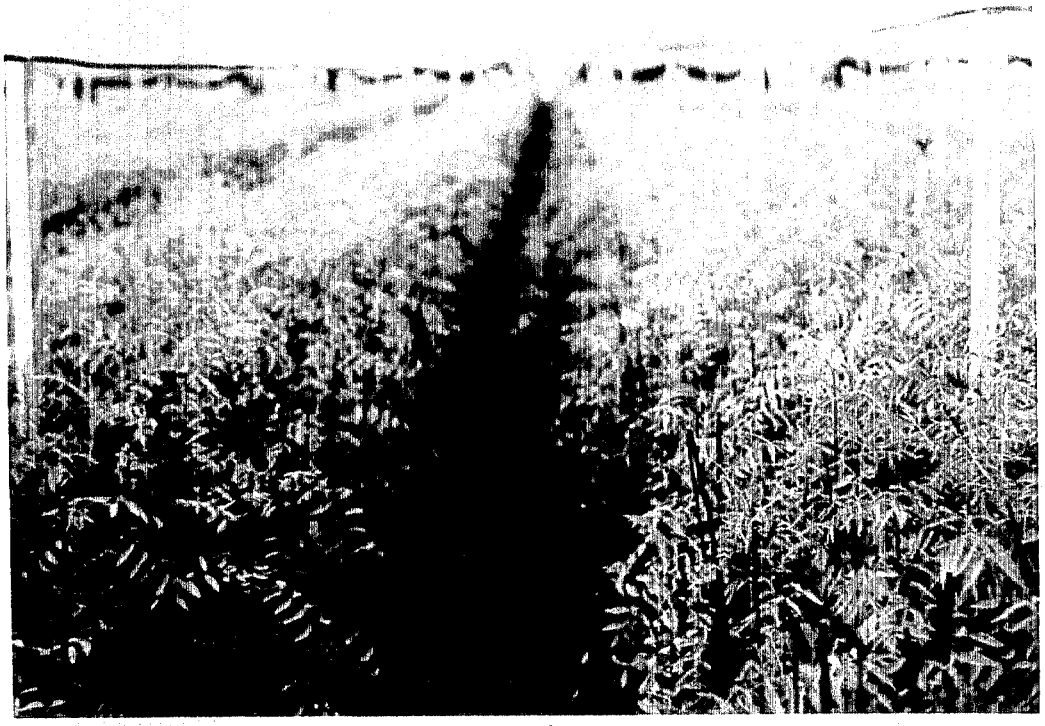
A
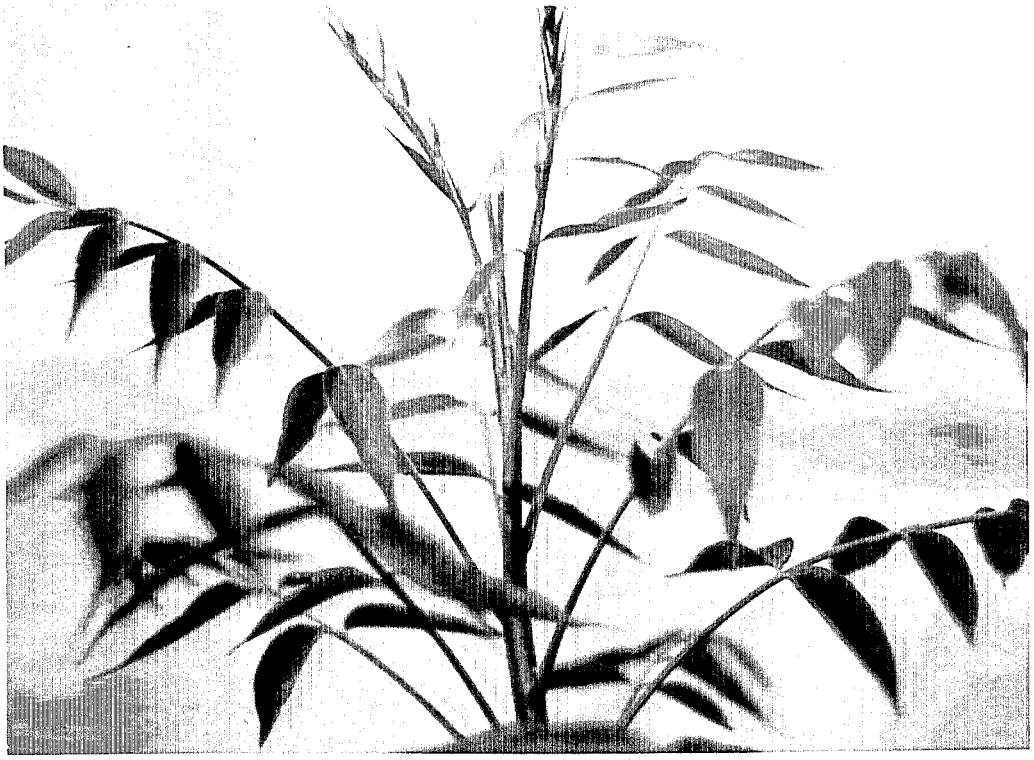
B

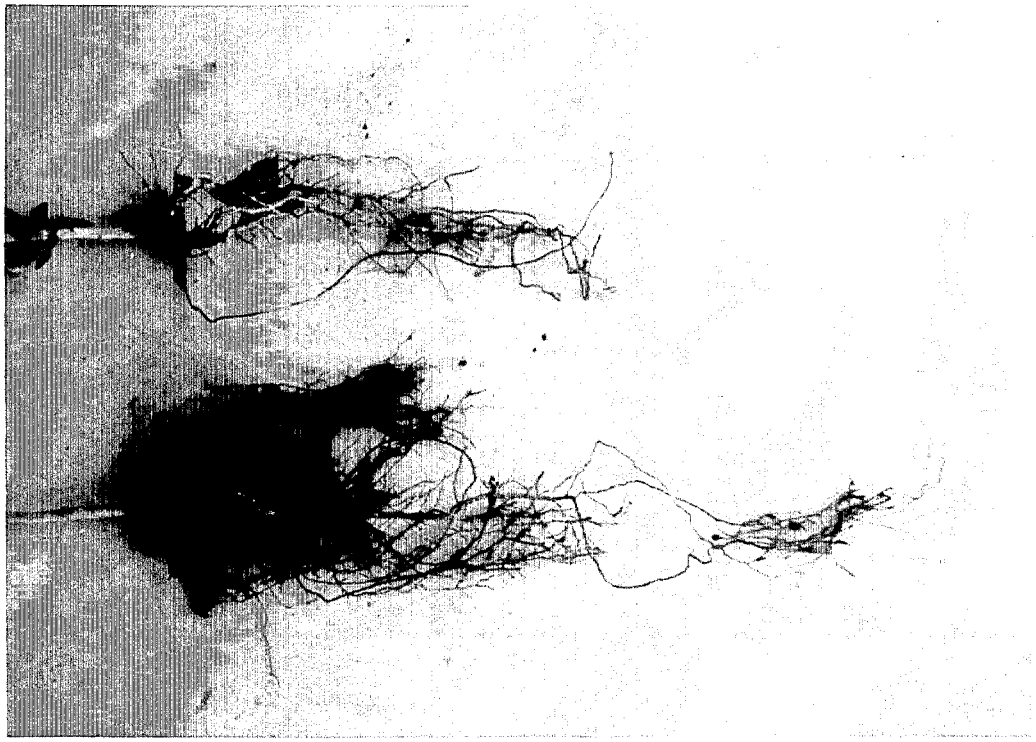
D
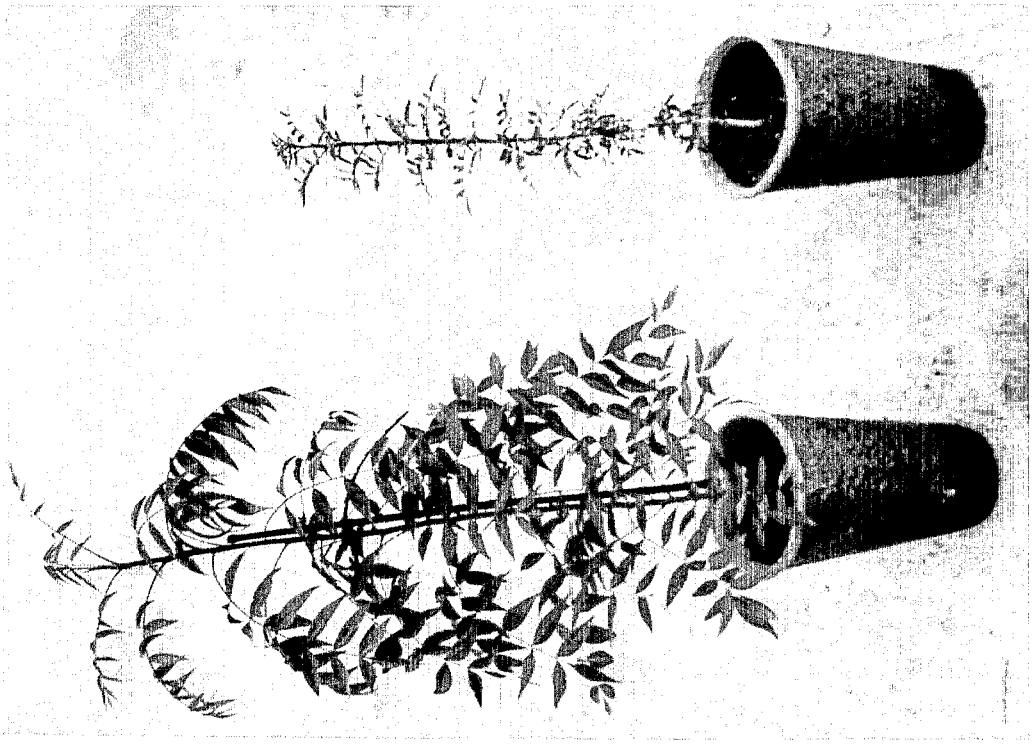
C